(12) United States Patent
Palcic et al.

(10) Patent No.: US 6,528,274 B1
(45) Date of Patent: *Mar. 4, 2003

(54) METHOD FOR THE PRODUCTION OF SIALYLATED OLIGOSACCHARIDES

(75) Inventors: Monica Marija Palcic, Edmonton (CA); Keiko Sujino, Edmonton (CA)

(73) Assignee: Synsorb Biotech, Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/390,281

(22) Filed: Sep. 3, 1999

Related U.S. Application Data

(63) Continuation-in-part of application No. 09/146,285, filed on Sep. 3, 1998, now Pat. No. 6,194,178.

(51) Int. Cl.$^7$ .............................. C12Q 1/48; C12P 19/18
(52) U.S. Cl. .............................. 435/15; 435/72; 435/74; 435/84; 435/97; 435/101
(58) Field of Search .............................. 435/97, 74, 72, 435/84, 101, 15

(56) References Cited

U.S. PATENT DOCUMENTS

| | | | |
|---|---|---|---|
| 4,727,136 A | 2/1988 | Jennings et al. | |
| 5,017,487 A | 5/1991 | Stunnenberg et al. | |
| 5,079,353 A | 1/1992 | Ratcliffe et al. | |
| 5,352,670 A | 10/1994 | Venot et al. | |
| 5,374,655 A | 12/1994 | Kashem et al. | |
| 5,384,249 A | 1/1995 | Sasaki et al. | |
| 5,461,143 A | * 10/1995 | Wong et al. | 536/17.5 |
| 6,194,178 B1 | * 2/2001 | Palcic et al. | 435/84 |

FOREIGN PATENT DOCUMENTS

| | | | |
|---|---|---|---|
| EP | 0 475 354 | 9/1991 | |
| WO | WO 93/18157 | 9/1993 | |
| WO | WO 95/04816 | 2/1995 | |
| WO | WO 96/32491 | 10/1996 | |
| WO | WO 97/18302 | * 5/1997 | C12N/9/10 |

OTHER PUBLICATIONS

Abbas et al., "Tumor–Associated Oligosaccharides 1: Synthesis of Sialyl–Lewis$^a$ Antigenic Determinant" *Proc. Japanese–German Symp.* Berlin, pp. 22–23 (1988).

Baisch et al., "Enzymatic Fucosylations with PurineDiphosphate–Fucoses (PDP–Fucosos)" *Bioorganic and Medicinal Chemistry Letters* 6(24):2953–2956 (1996).

Barsoum et al., "Production of Autoantibodies by Immunization with Rabbit Transferrin Modified at its Glycosidic Moiety" *Mol. Immunol.*, 18(5):367–372 (1981).

Baumberger et al., "Synthesis of N–Acetyl–4–deoxyneuraminic Acid" *Helv. Chem. Acta*, 69:1535–1541 (1986).

Beau et al., "Metabolism of 4–O–Methyl–N–acetylneuraminic Acid a Synthetic Sialic Acid" *Eur. J. Biochem.*, 106:531–540 (1980).

Bergh et al., "Aglycon specificity of fetal calf liver and ovine and porcine submaxillary gland α –N–acetylgalactosaminide α2→6 sialyltransferase" *Eur. J. Biochem.*, 136:113–118 (1983).

Beyer et al., "Glycosyltransferases and Their Use in Assesing Oligosaccharide Structure and Structure–Function Relationships" *Adv. Enzymol.*, 52:23–35 (1981).

Brandley et al., "Carbohydrate Ligands of the LEC Cell Adhesion Molecules" *Cell*, 63:861–863 (1990).

Brossmer et al., "Enzymic Synthesis of 5–Acetamido–9–Azido–3, 5, 9–Trideoxy–D–glycero–D—galacto–2–nonulosonic acid, a 9–Azido–9–Deoxy Derivative of N–Acetylneuraminic Acid" *Biochem. Biophys. Res. Comm.*, 96(3):1282–1289 (1980).

Christian et al., "On the Side–Chain Conformation of N–Acetylneuraminic Acid and its Epimers at C–7, C–8, and C–7,8" *Carbohydr. Res.*, 162:1–11 (1987).

Christian et al., "The Side–Chain Conformations of N–Acetyl–7–,8–,9–Deoxy–, and –4,7–DideoxyNeuraminic Acid and Their Effect on the Activation of CTP:N–Acylneuraminic Acid Cytidylyl–Transferase" *Carbohydr. Res.*, 194:49–61 (1989).

Conradt et al., "Preparation of 9–fluoro–9–deoxy–N–[2–$^{14}$C]acetylneuraminic acid Activation and transfer onto asialo–α$_1$–acid glycoprotein" *FEBS Lett.*, 170(2):295–300 (1984).

Conradt et al., *Japanese–German Symp.* pp. 104–105 Berlin (1988).

de Heij, et al., "Biosynthesis of Disalylated β–D–Galactopyranosyl–(1→3)–2–Acetamido–2–Deoxy–β–D–Glucopyranosyl Oligosaccharide Chains. Identification of the β–D–Galactoside α–(2→3) and a 2–Acetamido–2–deoxy–β–D–Glucoside α–(2→6)–Sialyltransferase in Regenerating Rat Liver and Other Tissue" *Carbohydr. Res.*, 149:85–99 (1986).

Feizi, "Carbohydrate differentiation antigens: probable ligands for cell adhesion molecules" *TIBS*, 16:84–86 (1991).

Fügedi et al., "Thioglycosides as Glycosylating Agents in Oligosaccharide Synthesis" *Glycoconj. J.*, 4:97–108 (1987).

Fung et al., "Active Specific Immunotherapy of a Murine Mammary Adenocarcinoma Using a Synthetic Tumor–associated Glycoconjugate" *Cancer Res.*, 50:4308–4314 (1990).

(List continued on next page.)

Primary Examiner—Francisco Prats
(74) Attorney, Agent, or Firm—Burns, Doane, Swecker & Mathis, LLP

(57) ABSTRACT

Disclosed are methods for the enzymatic synthesis of α-sialylated oligosaccharide glycosides. Specifically, in the disclosed methods, α2,3-sialyltransferase is used to transfer an analogue of sialic acid, employed as its CMP-nucleotide derivative, to the non-reducing sugar terminus of an oligosaccharide having a fucosyl group in the penultimate saccharide unit to the non-reducing sugar terminus. The analogue of sialic acid and the oligosacchairde employed in this method are selected to be compatible with the sialyltransferase employed.

2 Claims, No Drawings

OTHER PUBLICATIONS

Gokhale et al., "Chemical synthesis of GDP–fucose analogs and their utilization by the Lewis α(1→4) fucosyltransferase" *Can J. Chem.* 68(7):1063–1071 (1990).

Gross et al., "N–Acetyl–4–deoxy–D–neuraminic Acid is Activated and Transferred on to Asialoglycoprotein" *Glycoconj. J.,* 4:145–156 (1987).

Gross et al., "Activation and transfer of novel synthetic 9–substituted sialic acids" *Eur. J. Biochem.,* 168:595–602 (1987).

Gross et al., "Interaction of N–Acetyl–4–epi–D–neuraminic Acid with Key Enzymes of Sialic Acid Metabolism" *Biochemistry,* 27:4279–4283 (1988).

Gross et al., "Enzymatic introduction of a fluorescent sialic acid into oligosaccharide chains of glycoproteins" *Eur. J. Biochem.,* 177:583–589 (1988).

Gross et al., "Inhibition of N–acetylneuraminate lyase by N–acetyl–4–oxo–D–neuraminic acid" *FEBS Lett.,* 232(1):145–147 (1988).

Hagedorn et al., XIIIth Carbohydr. Symp., Ithaca (1986) A4.

Hakomori, Sen–itiroh, "Aberrant glycosylation in tumors and tumor–associated carbohydrate antigens" *Adv. Cancer Res.,* 52:257–263 (1989).

Handa et al., "Modification of Sialic Acid Carboxyl Group of Ganglioside" *J. Biochem.,* 95(5):1323–1329 (1984).

Hasegawa et al., "Synthetic Studies on Sialoglycoconjugates 4: Synthesis of 5–Acetamido–3,5–Dideoxy–D–Galacto–2–Octulosonic Acid Derivatives and Analogs" *J. Carbohydr. Chem.,* 8(1):135–144 (1989).

Hasegawa et al., "Synthetic Studies on Sialoglycoconjugates 7: Synthesis of N–Acetylneuraminic Acid Derivatives and Analogs" *J. Carbohydr. Chem.,* 8(4):579–583, 596 (1989).

Haverkamp et al., "Improved Synthesis of CMP–Sialates Using Enzymes from Frog Liver and Equine Submandibular Gland" *Hoppe–Seyler's Z. Physiol. Chem.,* 360:159–166 (1979).

Henningsson et al., "T cell recognition of a tumor–associated glycoprotein and its synthetic carbohydrate epitopes: stimulation of anticancer T cell immunity in vivo" *Cancer Immunol. Immunother.,* 25:231–241 (1987).

Higa et al., "Sialylation of Glycoprotein Oligosaccharides with N–acetyl–, N–glycolyl, and N–O–Diacetylneuraminic Acids" *J. Biol. Chem.,* 260(15):8838–8849 (1985).

Horowitz, The Glycoconjugates, Index to vol. I, New York Academic Press (1977, 1978, 1982, 1983).

Houghton et al., *Symposium on Gangliosides and Cancer,* pp. 233–237, VCH Publishers (1988).

Howard, "Towards Better Carbohydrate Vaccines"; Proceedings of a meeting organized by the World Health Organization, R. Bell, G. Torrigani, Editors, pp. 212–236, Wiley, Chichester (1987).

Irie et al., *Symposium on Gangliosides and Cancer,* pp. 247–257, VCH Publishers (1988).

Joziasse et al., "Purification and Enzymatic Characterization of CMP–sialic Acid: β–Galacotsyl1→3–N–Acetylgalactosaminide α2→3–Sialyltransferase from Human Placenta" *J. Biol. Chem.,* 260(8):4941–4951 (1985).

Kameyama et al., "Total Synthesis of sialyl Lewis X" *Carbohydr. Res.,* 209:c1–c4 (1991).

Le et al., "Analysis by capillary electrophoresis–laser–induced fluorescence detection of oligosaccharides produced from enzyme reactions" *J. Chromatography A.* 716:215–220 (1995).

Livingston et al., "Vaccines containing purified GM2 ganglioside elicit GM2 antibodies in melanoma patients" *Proc. Natl. Acad. Sci.* (USA), 84:2911–2915 (1987).

Mack et al., "Synthesis of 6–Thiosialic Acids and 6–Thio–N–Acetyl–D–Neuraminic Acid" *Tetrahedron Lett.,* 28(2):191–194 (1987).

Nakajima et al., "Synthesis of N–Acetyl–3–fluoro–neuraminic Acids" *Agric. Biol. Chem.,* 52(5):1209–1215 (1988).

Nakamura et al., "Biochemical Properties of N–Methylamides of Sialic Acids in Gangliosides" *J. Biochem,* 99(1):219–226 (1986).

Naor et al., "Immune Response to Chemically Modified Antigens" *Prog. Allergy,* 22:107–146 (1977).

Okamoto et al., "Glycosidation of Sialic Acid" *Tetrahedron,* 46(17):5835–5839 (1990).

Ørskov et al., "Form variation in *Escherichia Coli* K1: Determined by O–Acetylation of the Capsular Polysaccharide" *J. Exp. Med.,* 149:669–685 (1979).

Paulsen, "Advances in Selective Chemical Syntheses of Complex Oligosaccharides" *Angewandte Chemie* Intl. Ed. Eng., 21(3):155–157, 170–173 (1982).

Paulsen et al., "Synthese von α–D–glycero–D–galacto–2–Octulonsäure und 5–Acetamido–5–desoxy–β–D–erythro–L–gluco–2–nonulonsäure" *Liebigs Ann. Chem.,* pp. 277–279 (1988).

Paulson et al., "Purification of a Sialyltransferase from Bovine Colostrum by Affinity Chromatography on CDP–agarose" *J. Biol. Chem.,* 252(7):2356–2362 (1977).

Paulson et al., "Biosynthesis of a disialylated sequence in N–linked oligosaccharides: identification of an N–acetylglucosaminide (α2→6)–sialyltransferase in Golgi apparatus from rat liver" *Eur. J. Biochem.,* 140:523–530 (1984).

Paulson, "Interactions of Animal Viruses with Cell Surface Receptors" *The Receptors,* vol. II Conn Ed., N.Y. Acad. Press, pp. 131–219 (1985).

Reuter et al., "Suggestions on the Nomenclature of Sialic Acids" *Glycoconjugate J.,* 5:133–135 (1988).

Sadler et al., "Purification to Homogeneity of a β–Galactoside α–2→ 3 Sialyltransferase and Partial Purification of an α–N–Acetylgalactosaminide α 2→ 6 Sialyltransferase from Porcine Submaxillary Glands" *J. Biol. Chem.,* 254(11):4434–4442 (1979).

Sadler, "Purification to Homogeneity and Enzymatic Characterization of an α– N–Acetylgalactosaminide α 2→ 6 Sialyltransferase from Porcine Submaxillary Glands" *J. Biol. Chem.,* 254(13):5934–5941 (1979).

Salunkhe et al., "A new useful approach to the Epimers at C–7 and C–7,8 of N–Acetylneuraminic Acid" *Liebigs Ann. Chem.,* pp. 187–189 (1988).

Schauer, R., "Sialic Acids; Chemistry, Metabolism, and Function" *Cell Biology Monographs,* vol. 10, Springer–Verlag (1982).

Schengrund et al., "Binding of *Vibrio cholera* Toxin and the Heat–labile Enterotoxin of *Escherichia coli* to $G_{M1}$, Derivatives of $G_{M1}$, and Nonlipid Oligosaccharide Polyvalent Ligands" *J. Biol. Chem.,* 264(22): 13233–13237 (1989).

Schmidt, "New Methods for the Synthesis of Glycosides and Oligosaccharides– Are There Alternatives to the Koenigs–Knorr Method?" *Agnew. Chem. Int. Ed. Engl.,* 25:212–215, 232–235 (1986).

Sharma et al., "General Methods for Modification of Sialic Acid at C–9. Synthesis of N–Acetyl–9–Deoxy–9–Fluoroneuraminic Acid" *Carbohydr. Res.,* 175:25–34 (1988).

Srivastava et al., "Enzymatic Transfer of a Preassembled Trisaccharide Antigen to Cell Surfaces Using a Fucosyltransferase" *J. Biol. Chem.* 267(31):22356–22361 (1992).

Stangier et al., "Fucosyltransferase–catalyzed formation of L–galactosylated Lewis structures" *Carbohydrate Res.* 305:511–515 (1998).

Toone et al., "Enzyme–Catalyzed Synthesis of Carbohydrates" *Tetrahedron,* 45(17):5365–5369 (1989).

Weinstein et al., "Purification of a Galβ1→4GlcNAc α2→6 Sialyltransferase and a Galβ1→3(4)GlcNAc α2→3 Sialyltransferase to Homogeneity from Rat Liver" *J. Biol. Chem.,* 257(22):13835–13844 (1982).

Zbiral et al., "Strukturelle Abwandlungen an N–Acetylneuraminsäure, $3^1$ Synthese von 7–epi–, 8–epi und 7,8–Bis–epi–N–Acetylneuraminsäure– ihr Verhalten gegenüber Cytidin–Monophosphat–Sialinsäuresynthetase" *Monatsh. Chem.,* 116:87–91 (1985).

Zbiral et al., "Strukturelle Abwandlungen an N–Acetylneuraminsäuren, 8[1] Synthase von 7–, 8–, 9–Desoxy– und 4,7–Didesoxyneuraminsäure" *Monatsh. Chem.,* 119:127–131 (1988).

Zbiral et al., "Synthesis of the 4–acetamido–4–deoxy analogue of N–acetylneuraminic acid and its behaviour towards CMP–sialate synthase" *Carbohydr. Res.,* 194:c15–c18 (1989).

Gillespie W. et al., (1992) "Cloning and Expression of the Galβ1,3GalNAc α2,3–Sialyltransferase" *J. Biol. Chem.* 267(29):21004–21010.

Sasaki et al., (1993) "Expression Cloning of a Novel Galβ(1–3/1–4) GlcNac α2,3–Sialyltransferase Using Lectin Resistance Selection" *J. Biol. Chem.* 268(30):22782–22787.

Lee Y–C et al. (1994) "Cloning and Expression of cDNA for a New Type of Galβ1,3 GalNAc α2,3–Sialyltransferase", *J. Biol. Chem.* 269(13):10028–10033.

Goebel S.J. et al., (1990), "The Complete DNA Sequence of Vaccinia Virus" *Virology* 179(1):247–266.

Esposito (1991) "Properties of the Virus Particle", *Archives of Virology* (Suppl) 2:91–102.

Gross et al. (1990) "A Highly Sensitive Fluorometric Assay for Sialyltransferase Activity Using CMP–9–fluoresceinyl–NeuAc as Donor" *Analytical Biochem* 186:127–134.

McFadden, G. (1988) "Poxviruses of Rabbits" In "Virus Diseases in Laboratory and Captive Animals" Ed. G. Darai, Martinus Nijhoff Publishers Boston 36–62.

Russell, R.J. and Robbins, S.J. (1989) "Cloning and Molecular Characterization of the Myxoma Virus Genome", *Virology* 170:147–159.

Mykytowycz (1953) "An Attentuated Strain of the Myxomatosis Virus Recovered From the Field", *Nature* 172:448–449.

Stamenkovic et al., (1990) "The B Cell Antigen CD75 is a Cell Surface Sialyltransferase" *J. Exp. Med.* 172:641–643.

Bast et al., (1992) "The HB–6, Cdw75, and CD76 Differentiation Antigens are Unique Cell–Surface Carbohydrate Determinants Generated by the β–Galactoside α2,6–Sialyltransferase" *J. Cell Biol.* 116(2):423–435.

Bouvier (1954) Quelques remarques sur la myxomatose *Bulletin de L'Office International des Epizooites* 46:76–77.

Jackson, R.J. and Bults, H.G (1992) "A myxoma virus intergenic transient dominant selection vector" *J. Gen Virol.* 73:3241–3245.

Sticher, U. et al., (1988) "Purification of α2,6–sialyltransferase from rat liver by dye chromatography" *Biochem J.* 253:577–580.

Kajihara et al., *J. Org. Chem.,* 61(24):8632–8635 (1996).

Palcic et al., *Methods Enzymol,* 230:300–316 (1994).

\* cited by examiner

METHOD FOR THE PRODUCTION OF SIALYLATED OLIGOSACCHARIDES

CROSS-REFERENCE TO RELATED APPLICATIONS

This application is a continuation-in-part of U.S. application Ser. No. 09/146,285, filed on Sep. 3, 1998 now U.S. Pat. No. 6,194,178 B1, which is incorporated by reference herein in its entirety.

BACKGROUND OF THE INVENTION

1. Field of the Invention

This application is directed to methods for the enzymatic synthesis of α-sialylated oligosaccharides. Specifically, in the methods of this invention α2,3-sialyltransferase is employed to transfer sialic acid or an analogue thereof, employed as its CMP-nucleotide, to the non-reducing terminus of an oligosaccharide which oligosaccharide has a fucosyl group in the position penultimate to the non-reducing sugar terminus of the oligosaccharide.

2. References

The following references are cited in this application as superscript numbers at the relevant portion of the application and are incorporated herein in their entirety.

1. Horowitz, The Glycoconjugates, Vols. I–V, Pigman, Editor New York Academic Press (1977, 1978, 1982, 1983)
2. Hakomori, Adv. Cancer Res., 52:257–331 (1989)
3. Venot et al., U.S. Pat. No. 5,352,670
4. Schengrund et al., J. Biol. Chem., 264: 13233–13237 (1989)
5. Paulson, "Interaction of Animal Viruses with Cell Surface Receptors" in The Receptors Conn Ed N.Y. Acad. Press, pp. 131–219 (1985)
6. Feizi, TIBS, 16:84–86 (1991)
7. Brandley et al., Cell, 63:861–863 (1990)
8. Houghton et al., Symposium on Gangliosides and Cancer, pp. 233–237, VCH Publishers (1988)
9. Irie et al., Symposium on Gangliosides and Cancer, pp. 247–257, VCH Publishers (1988)
10. Howard, in "Towards Better Carbohydrate Vaccines"; Proceedings of a meeting organized by the World Health Organization, R. Bell, G. Torrigani, Editors, pp. 212–236, Wiley, Chichester (1987).
11. Henningsson et al., Cancer Immunol. Immunother., 25:231–241 (1987)
12. Fung et al., Cancer Res., 50:4308–4314 (1990)
13. Livingston et al., Proc. Natl. Acad. Sci. (USA), 84:2911–2915 (1987)
14. Naor et al., Prog. Allergy, 22:107–146 (1977)
15. Orskov et al., J. Exp. Med., 149:669–685 (1979)
16. Barsoum et al., Mol. Immunol., 18:495–550 (1981)
17. Jennings et al., U.S. Pat. No. 4,727,136 (1985)
18. Honda et al., J. Biochem., (Tokyo) 95:1323–1329 (1984)
19. Nakamura et al., J. Biochem., (Tokyo) 99:219–226 (1986)
20. Reuter et al., Glycoconjugate J., 5:133–135 (1988)
21. Weinstein et al., J. Biol. Chem., 257:13835–13844 (1982)
22. Paulsen et al., J. Biol. Chem., 252:2356–2362 (1977)
23. Evans-Sadler et al., J. Biol. Chem., 254:4434–4443 (1979)
24. Conradt et al., Japanese-German Symp. pp. 104–105 Berlin (1988)
25. Joziasse et al., J. Biol. Chem., 260:4941–4951 (1985)
26. Evans-Sadler, J. Biol. Chem., 254:5934–5941 (1979)
27. Bergh et al., Eur. J. Biochem., 136:113–118 (1983)
28. Higa et al., J. Biol. Chem., 260:8838–8849 (1985)
29. Paulsen et al., Eur. J. Biochem., 140:523–530 (1984)
30. de Heij et al., Carbohydr. Res., 149:85–99 (1986)
31. Sialic Acids in "Cell Biology Monographs" Schauer, Editor, Vol. 10 (1982)
32. Okamoto et al., Tetrahedron, 46, No. 17, pp. 5835–5837 (1990).
33. Ratcliffe et al., U.S. Pat. No. 5,079,353, (1987).
34. Abbas et al., Proc. Japanese-German Symp. Berlin, pp. 20–21 (1988).
35. Paulsen, Agnew. Chem. Int. Ed. Eng., 21:155–173 (1982).
36. Schmidt, Agnew. Chem. Int. Ed. Eng., 25:212–235 (1986).
37. Fugedi et al., Glycoconj. J., 4:97–108 (1987).
38. Kameyama et al., Carbohydr. Res., 209:C.sub.1–C.sub.4 (1991).
39. Brossmer et al., Biochem. Biophys. Acta., 96:1282–1289 (1980)
40. Gross et al., Eur. J. Biochem., 168:595–602 (1987)
41. Zbiral et al., Monatsh. Chem., 119:127–141 (1988)
42. Sharma et al., Carbohydr. Res., 175:25–34 (1989)
43. Hasegawa et al., J. Carbohydr. Chem., 8:579–588 (1989)
44. Zbiral et al., Monatsh. Chem., 116:87–98 (1985)
45. Salunkle et al., Liebigs Ann. Chem., pp. 187–189 (1988)
46. Hasegawa et al., J. Carbohydr. Chem., 8:135–144 (1989)
47. Gross et al., Biochemistry, 27:4279–4283 (1989)
48. Zbiral et al., Carbohydr. Res., 194:C15–C18 (1989)
49. Gross et al., FEBS Lett., 232:145–147 (1988)
50. Paulsen et al., Liebigs Ann. Chem., pp. 277–279 (1988)
51. Nakajimna et al., Agric. Biol. Chem., 52:1209–1215 (1988)
52. Baumberger et al., Helv. Chem. Acta, 69:1535–1541 (1986)
53. Beau et al., Eur. J. Biochem., 160:531–540 (1980)
54. Mack et al., Tetrahedron Lett., 28:191–194 (1987)
55. Gross et al., Eur. J. Biochem., 177:583–589 (1988)
56. Christian et al., Carbohydr. Res., 194:49–61 (1989)
57. Conradt et al., FEBS Lett., 170:295–300 (1984)
58. Christian et al., Carbohydr. Res., 162:1–11 (1987)
59. Haverkamp et al., Hoppe-Seyler's Z. Physiol. Chem., 360:159–166 (1979)
60. Gross et al., Glycoconj. J., 4:145–156 (1987)
61. Hagedorn et al., XIIIth Carbohydr. Symp., Ithaca (1986) A4
62. Toone et al., Tetrahedron, No. 17, 45:5365–5422 (1989)
63. Palcic, Methods in Enzymology 230:300 (1994)
64. Beyer et al., Adv. Enzymol., 52:24–158 (1981)
65. International Patent Application Publication No. WO97/18302
66. Le et al., J. Chromatography 781:515–522 (1997)
67. Kashem et al., U.S. Pat. No. 5,374,655
68. Gokhale et al., Can J. Chem. 68:1063 (1990)
69. Srivastava et al., J. Biol. Chem. 267:22356–22361 (1992)
70. Stangier et al., Carbohydrate Res. 305:511–515 (1998)
71. Baisch et al., Bioorganic and Medicinal Chemistry Letters 6:2953–2956 (1996)

3. State of the Art

Carbohydrates and/or oligosaccharides are present on a variety of natural and pathological glycoconjugates[1]. Of particular interest are carbohydrates and oligosaccharides containing sialic acid residues particularly at the nonreducing sugar terminus[31]. Such sialic acid terminated carbohydrates and oligosaccharides are present in a number of products which have been implicated in a wide range of biological phenomena based, in part, on the concept of recognition signals carried by the carbohydrate structures and by their binding to specific ligands.

Specifically, such sialic acid terminated carbohydrates and oligosaccharides are believed to be receptors for the binding of toxins[4], pathogenic agents such as viruses[5], and are believed to be recognition sites for a variety of lectins, particularly those involved in cellular adhesion[6,7], etc.

Similarly, certain oligosaccharides including sialic acid terminated oligosaccharides have been identified as capable of suppressing a cell-mediated immune response to an antigen. The ability of such oligosaccharides to suppress a cell mediated immune response to an antigen is described by Venot et al.[3]

Additionally, the presence of certain sialyl terminated oligosaccharides in tumor-related antigens is documented in the art[1] and, in general, the structures of the oligosaccharides present on such antigens have been modified in some way from normal oligosaccharides so as to lead to the expression of tumor related antigens[2]. The prospect of passive immunotherapy with monoclonal antibodies directed against some sialylated tumor-associated antigens, such as the gangliosides $GD_2$, $GD_3$ and $GM_2$, in patients with melanoma has been investigated[8,9].

The synthesis of such oligosaccharides often involves complex chemical reactions with corresponding low yields. Accordingly, there has been much interest in using glycosyltransferases in synthesizing at least a part of these molecules.

Glycosyltransferases are a highly polymorphic group of membrane-bound enzymes of endoplasmic reticulum and Golgi bodies that catalyze the transfer of a single monosaccharide unit from a nucleotide donor to the hydroxyl group of an acceptor saccharide in the biosynthesis of N-glycan (Asn-GlcNAc N-glycosidic linkage; GlcNAc, N-acetylglucosamine) and O-glycan (Ser/Thr-GalNAc, O-glycosidic linkage; GalNAc, N-acetylgalactosamine) moieties of glycoproteins and glycolipids.

The eukaryotic sialyltransferases comprise a family of glycosyltransferases that catalyze the transfer of N-acetylneuraminic acid (NeuAc), a sialic acid (SA), from CMP-SA to the non-reducing terminus of oligosaccharide chains of glycoconjugates. The addition of the sialic acid normally terminates oligosaccharide chain elongation except for polysialic chains found on neural cell adhesion molecule and gangliosides.

Known eukaryotic sialyltransferases involved in the synthesis of N- and O-glycan derivatives of the glycoprotien and glycolipid are summarized in Table 1, dapted from Palcic[63]. In the table, the R represents the remainder of the acceptor glycoprotein, glycolipid or oligosaccharide chain.

TABLE 1

| sialyltransferase (SL) | EC Number | Linkage Synthesized |
| --- | --- | --- |
| Gal(2–6)-ST (ST6N) | 2.4.99.1 | NeuAcα2→6Galβ1→4GlcNAc-R |
| GalNACα(2–6)-ST (ST6OI) | 2.4.99.4 | NeuACα2→6GalNAcα-R |
| Gal(2–3)-ST (ST3O) | 2.4.99.4 | NeuACα2→3Galβ1→4GalNAcα-R |
| Gal(2–3)-ST (ST3N) | 2.4.99.6 | NeuAcα2→3Galβ1→3/4GlcNAc-R |
| GalNAcα(2–6)-ST (ST6OII) | 2.4.99.7 | NeuAcα2→6<br>\|<br>NeuAcα2→3Galβ1→3GalNAc-R |

TABLE 1-continued

| sialyltransferase (SL) | EC Number | Linkage Synthesized |
| --- | --- | --- |
| N-Ac-neuramide α(2–8)-sialyltransferase | 2.4.99.8 | NeuAcα2→8NeuAcα2→Galβ-R |
| Galβ1-3GlcNAc-ST | | NeuAcα2→3Galβ1→3GlcNAc-R |

α2,3-sialyltransferases are useful eukaryotic enzymes for in vitro synthesis of N-linked and O-linked sialyl derivatives of glycoproteins, for determinations of acceptors, and other qualitative and quantitative research of glycoproteins. However, it was previously reported that 2,3-sialyltransferases would not synthesize N-linked and O-linked sialyl derivatives of glycoproteins or glycolipids where the acceptor glycoprotein or glycolipid possessed a fucosyl derivative in the penultimate position to the non-reducing sugar terminus of the oligosaccharide (U.S. Pat. No. 5,374,655[67]). This necessitated careful planning in the synthesis of certain fucosylated and sialylated oligosaccharides and in some cases required that certain steps be completed using chemical synthesis, rather than enzymatic synthesis.

In view of the above, it would be particularly advantageous to develop methods for the facile preparation of α-sialylated oligosaccharides from oligosaccharides having a fucosyl derivative in the penultimate position to the non-reducing sugar terminus of the oligosaccharide. The present invention accomplishes this by using an α2,3-sialyltransferase to effect efficient coupling of sialic acid activated as its CMP-nucleotide derivative (a donor saccharide) to a saccharide or an oligosaccharide having a fucosyl derivative in the penultimate position of the non-reducing end of the sugar moiety (acceptor oligosaccharide).

SUMMARY OF THE INVENTION

The present invention is directed to methods for the synthesis of oligosaccharides, glycoproteins and glycolipids terminated in the non-reducing sugar end by an analogue of N-acetylneuraminic acid. In particular, the methods of this invention employ α2,3-sialyltransferases to transfer a sialic acid or analogue thereof, activated as their CMP-nucleotide derivatives, to the non-reducing terminus of oligosaccharide acceptors.

Accordingly, in one of its method aspects, the present invention is directed to a method for the enzymatic synthesis of an α-sialylated and fucosylated oligosaccharide containing a sialic acid or analogue thereof which method comprises the steps of:

a) selecting a sialyltransferase compatible with a fucosylated oligosaccharide having a fucose group in the non-reducing penultimate saccharide position;

b) selecting a CMP-sialic acid or an analogue thereof which is compatible with the sialyltransferase selected in step (a);

c) contacting said CMP-sialic acid or an analogue thereof with a fucosylated oligosaccharide of the formula

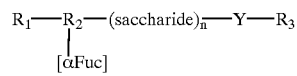

wherein $R_1$ represents a saccharide residue, $R_2$ represents a saccharide residue, and $R_1$ and $R_2$ together represent an acceptor for the selected sialyltransferase; n is from 0 to about 10, Y is selected from the group consisting of O, NH and S, and $R_3$ is selected from the group consisting of H, a protein, a lipid or an aglycon moiety having at least one carbon atom, in the presence of the sialyltransferase selected in step (a) above under conditions whereby the sialic acid or analogue thereof is transferred from the CMP-sialic acid or analogue thereof to the non-reducing sugar terminus of the fucosylated oligosaccharide so as to form an α-sialylated fucosylated oligosaccharide containing a sialic acid or analogue thereof.

This invention is also directed to a method for the enzymatic synthesis of a fucosylated and α-sialylated oligosaccharide which method comprises the steps of:

a) selecting a sialyltransferase capable of sialylating an oligosaccharide having a fucose group in the non-reducing penultimate saccharide position;

b) selecting a fucosyltransferase;

c) selecting a CMP-sialic acid or an analogue thereof which is compatible with the sialyltransferase selected in step (a);

d) selecting a GDP-fucose or an analogue thereof which is compatible with the fucosyltransferase selected in step (b);

e) contacting said CMP-sialic acid or an analogue thereof and said GDP-fucose or an analogue thereof with an oligosaccharide of the formula

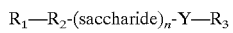

$R_1$—$R_2$-(saccharide)$_n$-Y—$R_3$ wherein $R_1$ represents a saccharide residue, $R_2$ represents a saccharide residue, and $R_1$ and $R_2$ together represent an acceptor for the selected sialyltransferase and the selected fucosyltransferase; n is from 0 to about 10, Y is selected from the group consisting of O, NH and S, and $R_3$ is selected from the group consisting of H, a protein, a lipid or an aglycon moiety having at least one carbon atom, in the presence of said sialyltransferase and said fucosyltransferase selected in (a) and (b) above, under conditions whereby the sialic acid or analogue thereof and the fucose or analogue thereof are transferred from the CMP-sialic acid or analogue thereof and the GDP-fucose or analogue thereof, respectively, to the non-reducing sugar terminus of the oligosaccharide so as to form an α-sialylated fucosylated oligosaccharide.

This invention is also directed to a method for determining the non-reducing terminus structure of an unknown oligosaccharide acceptor, which method comprises the steps of:

a) contacting the oligosaccharide acceptor with a sialyltransferase which is not capable of sialylating a non-reducing terminus of an oligosachairde having a fucose group in the non-reducing penultimate saccharide position and determining whether the oligosaccharide was sialylated;

b) contacting the oligosaccharide with a sialyltransferase which is capable of sialylating a non-reducing terminus of an oligosachairde having a fucose group in the non-reducing penultimate saccharide position and determining whether the oligosaccharide was sialylated; and c) comparing the results to determine whether the non-reducing terminus was fucosylated. If the first aliquot of the unknown acceptor was not sialylated in step (a) and the second aliquot of acceptor was sialylated in step (b) then the acceptor was fucosylated in the non-reducing penultimate saccharide position.

DETAILED DESCRIPTION OF THE PREFERRED EMBODIMENTS

The present invention is directed to the discovery that certain α2,3-sialyltransferases will transfer compatible analogues of sialic acid to certain oligosaccharides, glycoproteins, and glycolipids having a fucosyl group in the penultimate position to the non-reducing end of the sugar. This discovery permits the synthesis of oligosaccharides α-sialylated at the non-reducing terminus from oligosaccharides having a fucosyl group in the penultimate position to the non-reducing end of the sugar. This method also permits the transfer of compatible analogues of sialic acid to the fucosylated oligosaccharide. This invention also permits the determination of the structure of acceptors and other qualitative and quantitive research of glycoproteins and glycolipids.

However, prior to discussing this invention in further detail, the following terms will first be defined.

A. Definitions

As used herein, the following terms have the definitions given below:

The term "sialic acid" means all of the naturally occurring structures of sialic acid including 5-acetoamido-3,5-dideoxy-D-glycero-D-galacto-nonulopyranosylonic acid ("Neu5Ac") and the naturally occurring analogues of Neu5Ac, including N-glycolyl neuraminic acid (Neu5Gc) and 9-O-acetyl neuraminic acid (Neu5,9Ac$_2$), which are compatible with the selected sialyltransferase. A complete list of naturally occurring sialic acids known to date are provided by Schauer[31].

Naturally occurring sialic acids which are recognized by a particular α2,3-sialyltransferase so as to bind to the enzyme and are then available for transfer to an appropriate acceptor oligosaccharide structure are said to be compatible with the sialyltransferase and are sometimes referred to herein as a "compatible naturally occurring sialic acid".

The term "analogues of sialic acid" refers to analogues of naturally occurring structures of sialic acid including those wherein the sialic acid unit has been chemically modified so as to introduce, modify and/or remove one or more functionalities from such structures. For example, such modification can result in the removal of an OH functionality, the introduction of an amine functionality, the introduction of a halo functionality, and the like. In so far as the sialic acid analogues are compatible with the sialyltransferase, they are sometimes referred to herein as a "compatible sialic acid analogues".

Certain analogues of sialic acid are known in the art and include, by way of example, 9-azido-Neu5Ac, 9-amino-Neu5Ac, 9-deoxy-Neu5Ac, 9-fluoro-Neu5Ac, 9-bromo-Neu5Ac, 8-deoxy-Neu5Ac, 8-epi-Neu5Ac, 7-deoxy-Neu5Ac, 7-epi-Neu5Ac, 7,8-bis-epi-Neu5Ac, 4-O-methyl-Neu5Ac, 4-N-acetyl-Neu5Ac, 4,7-di-deoxy-Neu5Ac, 4-oxo-Neu5Ac, 3-hydroxy-Neu5Ac, 3-fluoro-Neu5Ac acid as well as the 6-thio analogues of Neu5Ac. The nomenclature employed herein in describing analogues of sialic acid is as set forth by Reuter et al.[20]

Insofar as sialyltransferases are designed to transfer or donate compatible naturally occurring sialic acids, analogues of Neu5Ac are sometimes referred to herein as "artificial donors" whereas the compatible naturally occurring sialic acids are sometimes referred to herein as the "natural donors".

The term "sialyltransferase" refers to those enzymes which transfer a compatible naturally occurring sialic acid, activated as its cytidine monophosphate (CMP) derivative, to the terminal oligosaccharide structures of glycolipids or glycoproteins (collectively glycoconjugates) and include enzymes produced from microorganisms genetically modified so as to incorporate and express all or part of the sialyltransferase gene obtained from another source, including mammalian sources. Numerous sialyltransferases have been identified in the literature with the different sialyltransferases generally being distinguished from each other by the terminal saccharide units on the glycoconjugates which accept the transferase.[64] For example, sialyltransferases, which build the following terminal oligosaccharide structures on glycoconjugates have been characterized:

αNeu5Ac(2-3)βGal(1→3/4)βGlcNAc-[21]
αNeu5Ac(2-6)βGal(1-4)βGlcNAc-[21, 22]
αNeu5Ac(2-3)βGal(1-3)αGalNAc-[23]-25
αNeu5Ac(2-6)αGalNAc-[26]-28
αNeu5Ac(2-6)βGlcNAc-[29, 30].

Other sialyltransferases with a variety of specificities have been isolated from a variety of sources.

A "sialyltransferase compatible with a fucosylated oligosaccharide having a fucose group in the non-reducing penultimate saccharide position" means that the sialyltransferase is capable of sialylating an oligosaccharide having a fucose group or analogue thereof in the non-reducing penultimate saccharide position. It has been found that the myxoma virus α2,3-sialyltransferase, as disclosed in International Patent Application Publication No. WO97/18302[65], has this capability.

It is contemplated that related sialyltransferases also encoded by other genera of the sub-families of Chorodopoxvirinae, Entomopoxvirinae and the unclassified viruses of the family of Poxviridae will be compatible with a fucosylated oligosaccharide.

Analogues of sialic acid activated as their cytidinemonophosphate derivative which are recognized by a particular sialyltransferase so as to bind to the enzyme and are then available for transfer to an appropriate acceptor oligosaccharide structure are said to be compatible with the sialyltransferase and are sometimes referred to herein as a "compatible analogue of sialic acid". Because the transfer reaction employs a sialyltransferase, it goes without saying that an analogue of sialic acid employed in such a reaction must be a compatible analogue of sialic acid.

CMP-nucleotide derivative of Neu5Ac refers to the compound:

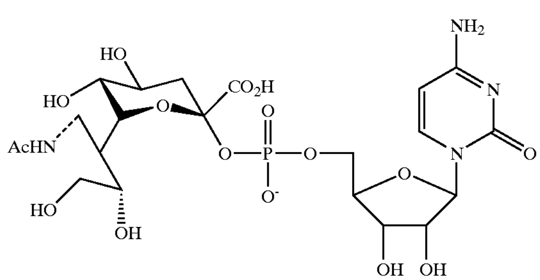

CMP Neu5Ac

CMP-derivatives of analogues of sialic acid refer to those compounds having structures similar to that above with the exception that the Neu5Ac residue is replace with an analogue of sialic acid.

The term "fucosyltransferase" refers to those enzymes which transfer a compatible naturally occurring fucose, activated as its guanosine diphosphate (GDP) derivative, to the terminal oligosaccharide structures of glycolipids or glycoproteins (collectively glycoconjugates) and include enzymes produced from microorganisms genetically modified so as to incorporate and express all or part of the fucosyltransferase gene obtained from another source, including mammalian sources. Numerous fucosyltransferases have been identified in the literature.

The term "analogues of fucose" refers to analogues of naturally occurring structures of fucose including those wherein the fucose unit has been chemically modified so as to introduce, modify and/or remove one or more functionalities from such structures. For example, such modification can result in the removal of an OH functionality, the introduction of an amine functionality, the introduction of a halo functionality, the introduction of a sulfate or phosphate moiety, and the like. Certain analogues of fucose are known in the art and include, by way of example, 3-deoxy-fucose[68], arabinose, C-6 modified fucoses[69] (i.e. 6-O-propyl fucose) and 3,6 dideoxy-L-galactose[70].

It is also contemplated that the fucose or analogues of fucose may be transferred from other purine diphosphates including, adenosine-5'-diphospho-fucose, xanthosine-5'-diphospho-fucose, inosine-5'-diphospho-fucose, etc.[71]

Analogues of fucose activated as their diphosphate derivative which are recognized by a particular fucosyltransferase so as to bind to the enzyme are then available for transfer to an appropriate acceptor oligosaccharide structure are said to be compatible with the fucosyltransferase. In so far as the fucose analogues are compatible with the fucosyltransferase, they are sometimes referred to herein as a "compatible fucose analogues".

The term "oligosaccharide" refers to compounds of the formula $$R_1—R_2\text{-(saccharide)}_n\text{-}Y—R_3$$

wherein $R_1$ represents a saccharide residue, $R_2$ represents a saccharide residue, and $R_1$ and $R_2$ together represent an acceptor for the selected sialyltransferase and the selected fucosyltransferase; n is from 0 to about 10, Y is selected from the group consisting of O, NH and S, and $R_3$ is selected from the group consisting of H, a protein, a lipid or an aglycon moiety having at least one carbon atom.

The term "fucosylated oligosaccharide" refers to compounds of the formula 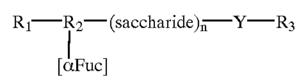 wherein $R_1$ represents a saccharide residue, $R_2$ represents a saccharide residue, and $R_1$ and $R_2$ together represent an acceptor for the selected sialyltransferase and the selected fucosyltransferase; n is from 0 to about 10, Y is selected from the group consisting of O, NH and S, and $R_3$ is selected from the group consisting of H, a protein, a lipid or an aglycon moiety having at least one carbon atom.

Since naturally occurring oligosaccharides and fucosylated oligosaccharides are acceptors for certain α2,3-sialyltransferases, and are believed to be acceptors of certain sialyltransferases in vivo, these oligosaccharides and fucosylated oligosaccharides are sometimes referred to herein as "natural acceptors". Contrarily, since the oligosaccharides and fucosylated oligosaccharides employed in this invention are sometimes different from such "natural acceptors", they are sometimes referred to herein as "artificial acceptors". That is to say that artificial acceptors are those oligosaccharides and fucosylated oligosaccharides which contain a substituent at the anomeric carbon atom of the reducing sugar which substituent is other than hydroxyl, a protein, or a lipid capable of forming a micelle or other large molecular weight aggregate. Accordingly, a protein linked to the anomeric carbon atom of the reducing sugar of the oligosaccharide or fucosylated oligosaccharide through its aglycon moiety would be an artificial acceptor since this acceptor contains an "artificial" unit, i.e., the aglycon linking group.

The fucosylated oligosaccharides of this invention may be further distinguished from natural acceptors by virtue of chemical modification(s) to one or more of the saccharide units of the oligosaccharide. Such chemical modification could involve the introduction and/or removal of one or more functionalities in one or more of the saccharide unit(s). For example, such modification can result in the removal of an OH functionality, the removal of saccharide unit(s), the introduction of an amine functionality, the introduction of a halo functionality, the introduction of one or more saccharide unit(s), and the like.

In a preferred embodiment, the aglycon moiety has from 1–20 carbon atoms and, more preferably, is selected from the group consisting of —(A)—Z' wherein A represents a bond, an alkylene group of from 2 to 10 carbon atoms, and a moiety of the form —($CH_2CR_4R_5G)_n(CH_2CR_4R_5$)— wherein n is an integer equal to 0 to 5; $R_4$ and $R_5$ are independently selected from the group consisting of hydrogen, phenyl, phenyl substituted with 1 to 3 substituents selected from the group consisting of amine, hydroxyl, halogen, alkyl of from 1 to 4 carbon atoms and alkoxy of from 1 to 4 carbon atoms, methyl, or ethyl; and G is selected from the group consisting of a bond, oxygen, sulphur, NH, and Z' is selected from the group consisting of hydrogen, methyl, —OH, —SH, —$NH_2$, —$NHR_6$, —$N(R_6)_2$, —C(O)OH, —C(O)$OR_6$, —C(O)$NHNH_2$, —C(O)$NH_2$, —C(O)$NHR_6$, —C(O)$N(R_6)_2$, and —$OR_7$ wherein each $R_6$ is independently alkyl of from 1 to 4 carbon atoms and $R_7$ is an alkenyl group of from 3 to 10 carbon atoms. Preferably, the —(A)—Z' group defines a group capable of being linked to a carrier or a group capable of being derivatized to a group which is capable of being linked to a carrier.

Preferably, the aglycon group is a hydrophobic group of at least 2 carbon atoms and more preferably at least 4 carbon atoms. Most preferably the aglycon group is —($CH_2)_8$COOMe.

When the aglycon group is one which is capable of being linked to a carrier such as an antigenic carrier, the methods of this invention are useful in preparing artificial conjugates such as artificial antigens having one or more α-sialylated oligosaccharide groups containing an analogue of sialic acid which groups are pendant to the antigen.

The carrier is a low or high molecular weight, nonimmunogenic or antigenic carrier including the linking to a fluorescent label, a radioactive label, biotin, or a photolabile linking arm or a moiety to be targeted. Preferably, the carrier is an antigenic carrier and accordingly, the artificial conjugate is an artificial antigen. In some cases it may be advantageous to employ a non-immunogenic carrier.

On the other hand, the carrier can be a low molecular weight carrier such as ethylene diamine, hexamethylene diamine, tris(2-aminoethyl)amine, L lysilysine, poly-L-lysine, and polymers of various molecular weights.

Saccharide units (i.e., sugars) useful in the oligosaccharides described above include by way of example, all natural and synthetic derivatives of glucose, galactose, N-acetylglucosamine, N-acetyl-galactosamine, fucose, sialic acid, 3-deoxy-D,L-octulosonic acid and the like. In addition to being in their pyranose form, all saccharide units in the oligosaccharides are in their D form except for fucose which is in its L form.

As noted above, oligosaccharides useful in the processes disclosed herein contain terminal units which are compatible with the selected sialyltransferase. That is to say that such compatible terminal units permit recognition of the oligosaccharide by a particular sialyltransferase so that the sialyltransferase binds to the oligosaccharide and further permits transfer of the compatible analogue of sialic acid onto the oligosaccharide.

B. Synthesis and Methodology
Preparation of Oligosaccharides

Oligosaccharides to which the sialic acid analogue is to be enzymatically coupled are readily prepared either by complete chemical synthesis or by chemical/enzymatic synthesis wherein glycosyltransferases (other than sialyltransferases) are employed to effect the sequential addition of one or more sugar units onto a saccharide or an oligosaccharide. Such methods are well known in the art. For example, chemical synthesis is a convenient method for preparing either the complete oligosaccharide glycoside; for chemically modifying a saccharide unit which can then be chemically or enzymatically coupled to an oligosaccharide glycoside; or for chemically preparing an oligosaccharide glycoside to which can be enzymatically coupled one or more saccharide units.

Chemical modifications of saccharide units are well known in the art which methods are generally adapted and optimized for each individual structure to be synthesized. In general, the chemical synthesis of all or part of the oligosaccharide first involves formation of a glycosidic linkage on the anomeric carbon atom of the reducing sugar. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, thioglycoside, etc. The donor is then reacted under catalytic conditions (e.g., a soluble silver salt such as silver trifluoromethanesulfonate, a Lewis acid such as boron trifluoride etherate or trimethylsilyltrifluoromethanesulfonate, or thioglycoside promoters such as methyl trifluoromethanesulfonate or dimethyl(methylthio)sulfonium trifluoromethanesulfonate) with an aglycon or an appropriate form of a carbohydrate acceptor which possess one free hydroxyl group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the oligosaccharide can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[32], Ratcliffe et al.[33], Abbas et al[34], Paulsen[35], Schmidt[36], Fugedi et al.[37], and Kameyama et al.[38]. The disclosures of each of these references are incorporated herein by reference in their entirety.

On the other hand, enzymatic coupling is accomplished by the use of glycosyl transferases which transfer sugar units, activated as their appropriate nucleotide donors, to specific saccharide or oligosaccharide acceptors, generally at the non-reducing sugar portion of the saccharide or oligosaccharide. See, for example, Toone et al.[62] and U.S. Pat. No. 5,374,655[67]. Moreover, it is possible to effect selected chemical modifications of the saccharide or oligosaccharide acceptor, of the sugar donor or the product of the enzymatic reaction so as to introduce modifications or further modifications into the structure.

Preparation of Analogues of Sialic Acid

Certain analogues of sialic acid are well known in the art and are prepared by chemical modification of sialic acid using procedures well documented in the art. For example, chemically modified Neu5Ac derivatives including 9-azido-Neu5Ac.[39], various 9-amino-Neu5Ac derivatives[40], 9-deoxy-Neu5Ac[41], 9-fluoro-Neu5Ac[42], 9-bromo-Neu5Ac[43], 8-deoxy-Neu5Ac[41], 8-epi-Neu5Ac[44], 7-deoxy-Neu5Ac[47]-epi-Neu5Ac[45], 7,8-bis-epi-Neu5Ac[45], 4-O-methyl-Neu5Ac[53], 4-N-acetyl-Neu5Ac[48], 4-epi-Neu5Ac[47], 4,7-di-deoxy-Neu5Ac[41], 4-oxo-Neu5Ac[49], 4-deoxy-Neu5Ac[52], 3-hydroxy-Neu5Ac[50], 3-fluoro-Neu5Ac[51] acid, the product of cleavage of the side chain at C-8 or at C-7[46] as well as the 6-thio analogues of Neu5Ac[54] are reported in the literature. Other sialic acid analogues are disclosed in U.S. Pat. No. 5,352,670[3]. Chemical modification leading to other sialic acid analogues would follow such established procedures.

Activation of Analogues of Sialic Acid to Their CMP—Nucleotide Derivatives

The enzymatic transfer of analogues of sialic acid require the prior synthesis (i.e., activation) of their nucleotide (CMP) derivatives. Activation of the analogues of sialic acid is usually done by using the enzyme CMP-sialic acid synthase which is readily available and the literature provides examples of the activation of various analogues of sialic acid such as 9-substituted Neu5Ac[28,39,40,55-57], 7-epiNeu5Ac[58], 7,8-bis-epi-Neu5Ac[58], 4-O-methyl-Neu5Ac[59], 4-deoxy-Neu5Ac[60], 4-acetamido-Neu5Ac[48], 7-deoxy-Neu5Ac[56], 4,7-dideoxy-Neu5Ac[56], the 6-thio derivatives of Neu5Ac[61] and Neu5OH (KDN). Still other examples of activated sialic acid analogues are disclosed in U.S. Pat. No. 5,352,670[3].

Transfer of the Analogues of Sialic Acid to the Oligosaccharide Acceptor

The nucleotide derivative of a compatible analogue of sialic acid and the compatible acceptor (i.e., a fucosylated oligosaccharide or an oligosaccharide having terminal saccharide unit(s) on the non-reducing end which are recognized by the selected sialyltransferase) are combined with each other in the presence of the selected sialyltransferase compatible with a fucosylated oligosaccharide under conditions wherein the sialic acid or analogue thereof is transferred to the acceptor. As is apparent, the saccharide or oligosaccharide acceptor employed must be one which functions as a substrate of the particular sialyltransferase employed.

In this regard, the art recognizes that artificial acceptors are tolerated in some cases by sialyltransferases especially where modification is in the aglycon part of the structure.

Likewise, when an analogue of sialic acid (i.e., an artificial donor) is to be enzymatically transferred, it is necessary that the CMP derivative of the analogue also be recognized by the sialyltransferase. In this regard, the art recognizes that certain sialyltransferases can tolerate some modifications to naturally occurring sialic acids and still transfer these analogues of sialic acid to glycoproteins or glycolipids possessing a suitable terminal acceptor structure.

It has been found that sialyltransferases possess sufficient recognition flexibility so as to transfer an artificial donor to an artificial acceptor[3]. Such flexibility permits the facile synthesis of a panel of oligosaccharides containing different analogues of sialic acid at the non-reducing sugar terminus of the oligosaccharide.

As noted above, a nucleotide derivative of a compatible sialic acid or a compatible analogue thereof is combined with a compatible acceptor (i.e., a saccharide or an oligosaccharide having terminal saccharide unit(s) on the nonreducing end which are recognized by the selected sialyltransferase) in the presence of the sialyltransferase under conditions wherein the sialic acid or analogue thereof is transferred to the acceptor. Suitable conditions, known in the art, include the addition of the appropriate sialyltransferase to a mixture of the compatible acceptor and of the CMP-derivative of the compatible sialic acid analogue in a appropriate buffer such as 0.1M sodium cacodylate in appropriate conditions of pH and temperature such as at a pH of 6.5 to 7.5 and a temperature between 25° and 45° C., preferably 35–40° C. for 12 hours to 4 days. The resulting oligosaccharide can be isolated and purified using conventional methodology comprising HPLC, ion exchange-, gel-, reverse-phase- or adsorption chromatography.

Once formed, the α-sialylated oligosaccharide glycoside can be further modified by chemical and/or enzymatic means to further derivatize this compound. For example, other glycosyltransferases can be used to add a glycosyl group to an α-sialylated oligosaccharide recognized by the transferase. This latter aspect is important insofar as the modifications made to the oligosaccharide must be compatible with the desired enzymatic transfers.

Additionally, the α sialylated oligosaccharide can be chemically modified to provide further derivatization of these compounds. Such chemical modification includes reduction of a 9-azido group on an analogue of sialic acid to an amine group which can be still further functionalized to another derivative such as the 9-acetamido derivative. Similarly, the carboxyl group found on analogues of sialic acid can be selectively transformed on α sialylated oligosaccharide glycosides via lactonization, reduction or transformation into an amide.

In one or more of the enzymatic steps recited above, the enzyme can be bound to a solid support so as to facilitate the reaction of the reagents and the recovery of the product from the enzyme.

C. Utility

The methods of this invention are useful in preparing oligosaccharides containing sialic acid or an analogue thereof bound via an α-linkage to the non-reducing sugar terminus of the oligosaccharide. Such oligosaccharides are recognized in the art as being useful as pharmaceuticals, as well as in the generation of antibodies to these structures, which antibodies are useful in diagnostic assays.

Additionally, methods of this invention are useful in preparing oligosaccharides containing an analogue of sialic acid bound via an α-linkage to the non-reducing sugar terminus of the oligosaccharide which can be coupled to an antigenic carrier so as to produce artificial antigens. Accordingly, such oligosaccharides act as intermediates in the preparation of artificial antigens.

Additionally, methods of this invention are useful in the determination of the non-reducing terminus of an unknown oligosaccharide. Specifically, a first aliquot of the unknown oligosaccharide acceptor can be contacted with a sialyltransferase which is not capable of sialylating a non-reducing terminus of an oligosaccharide having a fucose group in the non-reducing penultimate saccharide position and determining whether the oligosaccharide was sialylated; a second aliquot of the unknown oligosaccharide is also contected with an α-2,3 sialyltransferase which is capable of sialylating a non-reducing terminus of an oligosacchairde having a fucose group in the non-reducing penultimate saccharide position and determining whether the oligosaccharide was sialylated; the results are compared to determine whether the non-reducing terminus was fucosylated. If the first aliquot of the unknown acceptor was not sialylated and the second aliquot of acceptor was sialylated then the acceptor was fucosylated in the non-reducing penultimate saccharide position.

EXAMPLES

The following examples are offered to illustrate this invention and are not to be construed in any way as limiting the scope of this invention.

In these examples, unless otherwise defined below, the abbreviations employed have their generally accepted meaning:

| | |
|---|---|
| PBS | = phosphate buffered saline |
| MES | = morpholine ethane sulfonic acid |
| PMSF | = α-toluenesulfonyl fluoride |
| $Le^x$-gr | = 8-methoxycarbonyloctyl α-L-fucopyranosyl-(1→3)-[β-D-galactopyranosyl-(1→4)]-β-D-2-acetamide-2-deoxy-glucopyranoside |
| $Le^a$-gr | = 8-methoxycarbonyloctyl β-D-galactopyranosyl-(1→3) [α-L-fucopyranosyl-(1→4)]-β-D-2-acetamide-2-deoxy-glucopyranoside |
| CMP-NANA | = cytidine 5'-monophospho-N-acetyl-neuraminic acid |
| CMP-$^3$H-NANA | = cytidine 5'-monophospho-N-acetyl-neuraminic acid [sialic-9-$^3$H] |
| BSA | = bovine serum albumin |
| d | = doublet |
| dd | = doublet of doublets |
| s | = singlet |
| t | = triplet |
| GDP-Fuc | = guanosine-5'-diphospho-L-fucose |
| UDP-galactose | = uridine-5'-diphospho-galactose |
| TMR | = tetramethylrhodamine |

Commercially avaliable components are listed by manufacturer. Some of the recited manufacturers are as follows:
Millipore=Millipore Corp., Bedford Mass.
Waters=Waters Corp., Milford, Mass.
Boehringer Mannheim=Boehringer Mannheim, Laval, Quebec, Canada

Example 1
Preparation of Viral α2,3-sialyltransferase Cell Lysates

The myxoma viral α2,3-sialyl transferase cell lysate was prepared by a method similar to that set forth in International Patent Application Publication No. WO97/18302[65], which is incorporated herein by reference.

Ten T180 flasks of confluent layers of European rabbit kidney cell (RK13) cells were infected with Brazilian myxoma virus strain, Lausanne (Lu) (ATCC VR-115) isolated Campinas, Brazil, 1949 and Uriarra (Ur) isolated Australian Capital Territory, 1953 (a derivative of Moses strain (ATCC VR-116)). The cells were kept at 37° C. for 24 hours. Twenty-four hours post infection, the cells were detached by scraping and washed with PBS. Cell lysates were prepared by suspension in 20 mL of extraction buffer (50 mM MES, pH 6.1, 0.5% Triton-X100, 100 mM NaCl, 1.5 mM $MgCl_2$, 0.1 mM PMSF, 10 mg/ml aprotinin) at 4° C., for 45 minutes. The lysate was clarified by centrifugation at 2,000 g at 4° C. for 15 minutes.

The supernatant was recovered and applied to a 5 mL HiTrap Blue Affinity chromatography column (Pharmacia, Piscataway N.J.) in loading buffer (50 mM MES, pH6,1, 0.1% Triton-CF54, 100 mM NaCl, 25% glycerol). The α2,3-sialyltransferase was eluted from the column with a step NaCl elution (0.5 M, 1.0 M, 1.5 M, and 2.0 M NaCl). The α2,3-sialyltransferase was desalted by passing the eluant through a PD-10 column (BioRad, Hercules, Calif.) in column buffer (50 mM MES, pH 6,1, 0.1% Triton-CF54, 25% glycerol).

Total protein concentrations were measured using Bradford Bio-Rad and following the manufacturers instructions with IgG as a protein standard.

Example 2
Transfer of Sialic Acid to Lewis$^a$ and Lewis$^x$ ligosaccharide Acceptors Acceptor (54 nmol), CMP-NANA (40 nmol), and CMP-$^3$H-NANA (150,000–180,000 dpm) were added to a mixture of cell lysate (16 μL), water (3 μL) and 1 μL of assay buffer (250 mM MES, 0.5% Triton CF54, pH 7.0) in a 0.5 mL microfuge tube. Reaction mixtures were incubated at 37° C., diluted with water to 200 μL and loaded onto a $C_{18}$ Sep-Pak reverse-phase cartridge which had been pre-equilibrated with 20 mL of MeOH and 20 mL of water. The cartridge was washed with 50 mL of water and the product eluted with 4 mL of MeOH into a scintillation vial. The radioactivity of the MeOH eluates were quantitated by liquid scintillation in 10 mL of EcoLite (+) scintillation cocktail (ICN, Montreal, Quebec, Canada) in a Beckman liquid scintillation counter (LS1801).

Results of the radioactive transfer to the different acceptors in duplicate experiments were as follows:

| Acceptor | total CMP-NANA | Incubation time | dpm |
|---|---|---|---|
| $Le^x$-gr | 152644 | 90 min. | 1330/1130 |
| $Le^a$-gr | 176174 | 170 min. | 4161/4045 |

Example 3
Transfer of Sialic Acid to Various Oligosaccharide Acceptors

The ability of the isolated viral α2,3-sialyltransferase to transfer a sialic acid to various acceptors was tested.

Acceptor (54 nmol), CMP-NANA (40 nmol), and CMP-$^3$H-NANA (150,000–180,000 dpm) were added to a mixture of cell lysate (16 μL), water (3 μL) and assay buffer (250 mM MES, 0.5% Triton CF54, pH 6.1) in a 0.5 mL microfuge tube. Reaction mixtures were incubated at 37° C., diluted with water and measured by the method set forth in Example 2 above to obtain relative rates of transfer. Kinetics were carried out in an analogous method by varying the acceptor concentration from about 0.2×Km to 3×Km.

| Acceptor | Relative Rate (2.7 mM) | Km (μM) | Relative Vmax | rVmax/Km |
|---|---|---|---|---|
| LacNAc—O-gr | 100 | 112 ± 11 | 100 (1.5 nmol/mL/ | 0.896 |

-continued

| Acceptor | Relative Rate (2.7 mM) | Km (µM) | Relative Vmax | rVmax/Km (min) |
|---|---|---|---|---|
| 6',6'-C-dimethyl-LacNAc-O-octyl[1] | 17 | | | |
| Lactose-O-gr | 90 | 211 ± 40 | 112 | 0.531 |
| 3'-C-methyl-lactose-octyl[1] | 4.1 | | | |
| 4'-C-methyl-lactose-octyl[1] | 20 | | | |
| Le$^c$-O-gr | 79 | 202 ± 10 | 90 | 0.446 |
| T-disaccharide-O-gr | 64 | 427 ± 110 | 51 | 0.119 |
| Galα(1→3)-lacNAc-O-gr | 18 | | | |
| Galα(1→4)-lactose-O-gr | 12 | 9270 ± 1848 | 17 | 0.00183 |
| GlcNAc-O-gr | <1 | | | |
| Glc-O-octyl | <1 | | | |
| Gal-O-phenyl | <1 | | | |
| Fuc-Gal-O-octyl | 1.5 | | | |
| LacNAc-OH | 171 | | | |
| Lactose-OH | 121 | 97 ± 43 | 120 | 1.23 |
| Le$^a$-O-gr[1] | 50 | 1578 ± 105 | 42 | 0.0266 |
| Le$^x$-O-gr[1] | 21 | 9490 ± 1930 | 30 | 0.00316 |
| CMP-NANA | | 244 ± 36 | | |
| 7-LacNAc-O-gr[1] | 1.4 | | | | gr = (CH$_2$)$_8$ COOMe
CMP-NANA = cytidine 5'-monophospho-N-acetyl-neuraminic acid
[1]These compounds serve as acceptors for the viral α-2,3 sialyltransferase but are not acceptors for previously known mammalian α-2,3 sialyltransferase.

This indicates that the viral α2,3-sialyltransferase is able to use a number of different oligosaccharide structures as acceptors for the transfer of a sialic acid.

Example 4
Confirmation of 2,3 Linkage of Sialic Acid to Lewis$_a$ and Lewis$_x$ oligosaccharide Acceptors Le$^a$-TMR (35 nmol) and CMP-NANA (200 nmol) were incubated with viral cell lysate (4.9 µL) and alkaline phosphatase solution (0.1 µL) (5 µL of alkaline phosphatase (Boehringer Mannheim) 1000 U/ml and 1 µL BSA solution (100 mg/mL)). After gentle rotation at room temperature (25° C.) for 42 hours, additional alkaline phosphatase solution (0.2 µL) and CMP-NANA solution (100 mM, 0.2 µL) were added to the mixture which was reacted for 2 more days at room temperature. The reaction mixture was elevated and maintained at 37° C. for 48 hours, then the mixture was loaded onto a C$_{18}$-Sep-Pak cartridge (Waters) which had been pre-equilibrated with 10 mL of MeOH and 10 mL of water. The cartridge was washed with 5 mL of water then TMR-labeled compounds were eluted with 5 mL of MeOH. This solution was dried under vacuum, passed through a filter (Milliex-GV filter, 0.22 µm, Millipore Corp.) and lyophilized. Water was added to dry material to make 100 µM TMR concentration. This solution (0.5 µL) was mixed with capillary electrophoresis running buffer (10 mM phosphate, 10 mM sodium borate, 10 mM sodium dodecyl sulfate, 10 mM phenyl boronic acid pH 9.0, 499.5 µL). This solution was used for separation and analysis by capillary electrophoresis with laser induced fluorescence detection by the method set forth in Le et al.[66] A new product peak produced in the enzyme reaction had the same migration time as authentic sialylated Le$^x$-TMR and the new product peak was converted back to Le$^x$-TMR by treatment with neuraminidase.

Example 5
Preparative Synthesis of SialylLe$^x$-gr

Cell lysates (14 mL) were mixed with BSA solution (5 µL, 100 mg/mL). This solution was concentrated in a Slide-A-lyzer (Pierce Chemical Company, Rockford, Ill.) to 1.8 mL. Le$^x$-gr (4.7 mg, 6.7 µmol) and CMP-NANA (6.8 mg, 10.3 µmol) were added to 200 µL of concentrated cell lysate Alkaline phosphatase (Boehringer Mannheim, 1000 U/mL, 10 µL) was added. This reaction mixture was turned at room temperature for 24 days. During this incubation, CMP-NANA was added (6 times, after 3 days, 7 days, 11 days, 3.0 mg each, after 14 days, 18 days, 21 days, 2.0 mg each). This mixture was loaded onto a C$_{18}$-Sep-Pak Pak cartridge (Waters) which had been pre-equilibrated with 10 mL of MeOH and 10 mL of water. The cartridge was washed with 40 mL of water, then the product was eluted with 50 mL of 10% MeOH. This eluate was dried under vacuum and again loaded onto a C$_{18}$-Sep-Pak cartridge which had been pre-equilibrated with 10 mL of MeOH and 10 mL of water. After washing with water (10 mL); 1% MeOH (10 mL), and then 5% MeOH (10 mL), the desired product was eluted with 10% MeOH (17 mL). This solution was dried under vacuum, passed through a filter (Milliex-GV filter, 0.22 µm, Millipore Corp.) and lyophilized to give sialylated Le$^x$-gr (2.19 mg, 33%). The structure of the product sialyl Le$^x$-gr was confirmed by both NMR spectroscopy and mass spectrometry.

NMR (300 Hz, only typical peaks are shown, D$_2$O) δ5.10 (d, H, J=3.9 Hz, H-1(Fuc)), 4.51 (d, 2H, J=8.0 Hz, H-1(Gal, GlcNAc)), 3.69 (s, 3H, CO$_2$Me), 2.76 (dd, H, J=4.7, 12.6 Hz, H-3, (NANA)), 2.38 (t, 2H, J=11.4 Hz, CH$_2$CO$_2$Me), 2.04 (s,3H, Ac), 2.02 (s, 3H, Ac), 1.79 (t, H, J=12.2, 1.8 Hz, H-3 (NANA)), 1.17 (d, 3H, J=6.6 Hz, H-6 (Fuc)).

Mass calculated for C$_{41}$H$_{69}$N$_2$O$_{25}$=989.4; found 989.0

Sialylated Le$^a$-gr was also synthesized from Le$^a$-gr in a similar manner. Its structure was confirmed by both NMR spectroscopy and mass spectrometry.

NMR (300 Hz, only typical peaks are shown, D$_2$O) δ5.00 (d, H, J=3.9 Hz, H-1(Fuc)), 4.52 (d, 2H, J=7.7 Hz, H-1(Gal, GlcNAc)), 3.69 (s, 3H, CO$_2$Me), 2.76 (dd, H, J=4.7, 12.5 Hz, H-3, (NANA)), 2.39 (t, 2H, J=7.3 Hz, CH$_2$CO$_2$Me), 2.02 (s, 6H, Ac), 1.76 (t, H, J=12.3, H-3 (NANA)), 1.16 (d, 3H, J=6.4 Hz, H-6 (Fuc)).

Mass calculated for C$_{41}$H$_{69}$N$_2$O$_{25}$=989.4; found 989.0

Example 6
Synthesis of SialylLe$^x$-TMR from GlcNAc-TMR

GlcNAc-TMR (35 nmol), UDP-galactose (70 nmol), 0.5 µL isolated bovine milk β-1,4 galactosyltransferase (0.3 mU), GDP-fucose (70 nmol), 0.5 µL isolated human milk α1,3,4-fucosyltransferase (0.03 mU), CMP-NANA (100 nmol), 0.1 µL of 1 M MnCl$_2$ and 0.1 µL alkaline phosphatase (Boebringer Mannheim, 10 mU) were incubated with 5.7 µL of concentrated viral cell lysate solution. After gentle rotation at room temperature for 24 hours, 0.2 µL aliquots were removed and spotted onto a silica gel 60F$_{254}$ thin layer chromatography plate (Merck, Darmstadt Germany). The plate was developed with isopropanol:H$_2$O:NH$_4$OH (7:2:1). Le$^x$-TMR (Rf=0.18) and sialyl Le$^x$-TMR (Rf=0.30) were visible due to the pink chromophore TMR. These Rfs correspond to those of authentic material and the sialyl Le$^x$-TMR formed in the enzyme reaction mixture co-migrated with sialyl Le$^x$-TMR. The starting material GlcNAc-TMR (Rf=0.39) and the reaction intermediate LacNAc-TMR (Rf=0.25) were not detected.

Example 7
Synthesis of SialylLe$^a$-TMR from Le$^c$-TMR

Le$^c$-TMR (15 nmol), GDP-fucose (70 nmol), 0.5 µL isolated human milk, α-1,3,4-fucosyltransferase (0.03 mU), CMP-NANA (100 nmol), 0.1 µL of 1 M MnCl$_2$ and 0.1 µL alkaline phosphatase (Boehringer Mannheim, 10 mU) were incubated with 5.1 µL of concentrated viral cell lysate solution. After gentle rotation at room temperature for 72 hours, 0.2 μL aliquots were removed and spotted onto a silica gel 60F$_{254}$ thin layer chromatography plate (Merck, Darmstadt Germany). The plate was developed with isopropanol:H$_2$O:NH$_4$OH (7:2:1). Le$^a$-TMR (Rf=0.18) and sialyl Le$^a$-TMR (Rf=0.25) were visible due to the pink chromophore TMR. These Rfs correspond to those of authentic material and the sialyl Le$^a$-TMR formed in the enzyme reaction mixture co-migrated with sialyl Le$^a$-TMR. The starting material Le$^c$-TMR (Rf=0.31) was not detected.

What is claimed is:

1. A method for determining the non-reducing terminus structure of an unknown oligosaccharide acceptor, which method comprises the steps of:

a) contacting the oligosaccharide acceptor with a sialyltransferase which is not capable of sialylating a non-reducing terminus of an oligosaccharide having a fucose group in the non-reducing penultimate saccharide position and determining whether the oligosaccharide was sialylated;

b) contacting the oligosaccharide with an α-2,3 sialyltransferase which is capable of sialylating a non-reducing terminus of an oligosacchairde having a fucose group in the non-reducing penultimate saccharide position and determining whether the oligosaccharide was sialylated; and c) comparing the results to determine whether the non-reducing terminus was fucosylated.

2. The method according to claim 1, wherein step (c) comprises determining that the unknown acceptor was fucosylated in the non-reducing penultimate saccharide position where the acceptor was not sialylated in step (a) of claim 1 and was sialylated step (b) of claim 1.

* * * * *